US009579154B2

(12) United States Patent
Neri

(10) Patent No.: US 9,579,154 B2
(45) Date of Patent: Feb. 28, 2017

(54) SUPPORT DEVICE FOR PERCUTANEOUS INTERVENTION

(71) Applicant: Roberto Neri, Bracciano (IT)

(72) Inventor: Roberto Neri, Bracciano (IT)

(*) Notice: Subject to any disclaimer, the term of this patent is extended or adjusted under 35 U.S.C. 154(b) by 240 days.

(21) Appl. No.: 14/525,985

(22) Filed: Oct. 28, 2014

(65) Prior Publication Data
US 2016/0008071 A1    Jan. 14, 2016

(30) Foreign Application Priority Data

Jul. 9, 2014  (IT) .............................. RM2014A0371

(51) Int. Cl.
| | | |
|---|---|---|
| *A61B 19/10* | (2006.01) | |
| *A61G 13/10* | (2006.01) | |
| *A61B 19/02* | (2006.01) | |
| *A47B 1/05* | (2006.01) | |

(52) U.S. Cl.
CPC ............ *A61B 19/0256* (2013.01); *A47B 1/05* (2013.01); *A61B 46/23* (2016.02); *A61B 50/15* (2016.02); *A61B 50/20* (2016.02); *A61G 13/10* (2013.01); *A61G 13/105* (2013.01)

(58) Field of Classification Search
CPC ............... A61B 19/0256; A61B 46/30; A61B 2090/0436; A61B 50/15; A61B 50/20; A61B 46/23; A61G 13/105
USPC ... 5/621, 622, 623, 624, 648, 937, 943, 658; 108/146, 147.18, 148
See application file for complete search history.

(56) References Cited

U.S. PATENT DOCUMENTS

| | | | | | |
|---|---|---|---|---|---|
| 1,134,720 | A | * | 4/1915 | Bradley | ................ A61G 7/065 108/31 |
| 4,228,745 | A | * | 10/1980 | Gale | .................... A47C 16/025 108/116 |
| 5,174,453 | A | * | 12/1992 | Stoeffler | ............... A61B 50/33 206/370 |
| 5,601,036 | A | * | 2/1997 | Kieser | ..................... A47B 9/14 108/107 |
| 5,624,403 | A | * | 4/1997 | Jaquith | ................ A61M 25/02 128/DIG. 26 |
| D399,067 | S | * | 10/1998 | Harrison | ....................... D6/349 |
| 6,092,708 | A | * | 7/2000 | Rand | ...................... B60R 5/045 108/147.21 |
| 6,854,402 | B2 | * | 2/2005 | DuBarry | ................. A47B 1/08 108/137 |
| 7,060,046 | B2 | * | 6/2006 | Tanaka | .................. A61F 5/0193 5/621 |
| D566,987 | S | * | 4/2008 | Harrison | ................... D6/656.17 |
| 7,628,439 | B1 | | 12/2009 | Strong | |

(Continued)

FOREIGN PATENT DOCUMENTS

WO    2007048323 A1    5/2007

*Primary Examiner* — Michael Safavi
(74) *Attorney, Agent, or Firm* — Vivacqua Law, PLLC; Raymond J. Vivacqua; Steven L. Crane

(57) ABSTRACT

A device includes a support body with a substantially "C" squared-shape. The support body includes a support member and upright elements arranged on opposite sides of the support member that extend substantially orthogonally from the support member toward a surgical table. The device further includes one or more adjustment mechanisms connected to respective upright elements that adjust the spacing of the support member with respect to the surgical table to accommodate a patient's body positioned on the surgical table.

10 Claims, 1 Drawing Sheet

(56) References Cited

U.S. PATENT DOCUMENTS

Figure 1:
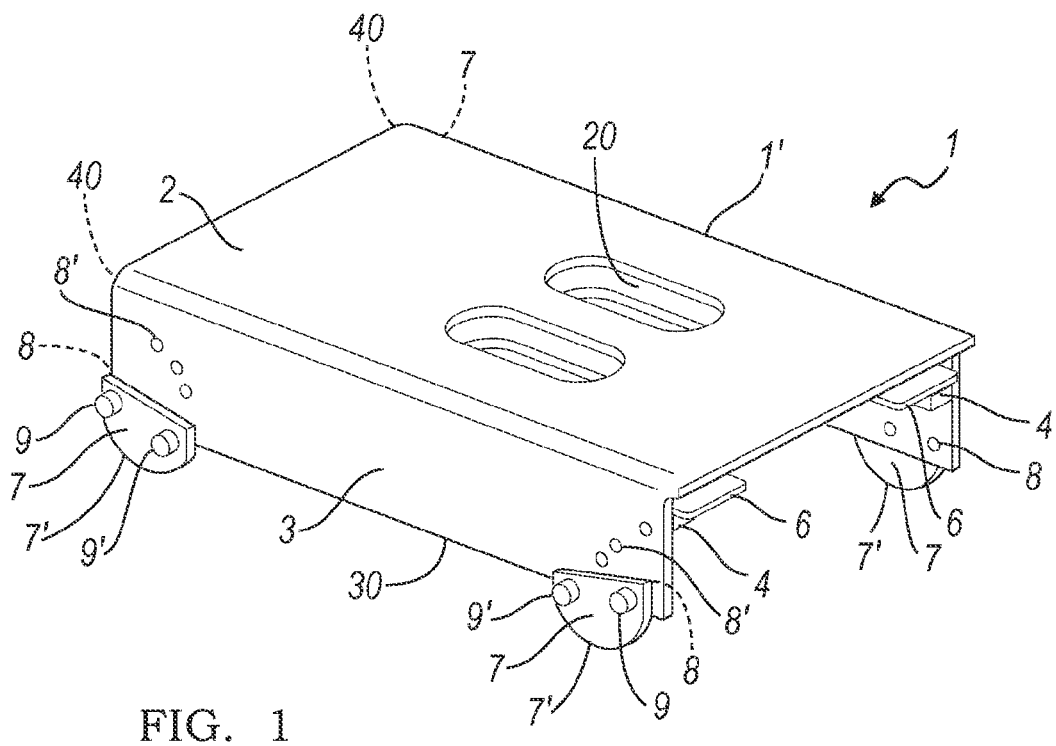

| | | | |
|---|---|---|---|
| 8,100,062 B1 | 1/2012 | Anghel | |
| 2006/0095066 A1* | 5/2006 | Chang | A61B 34/20 |
| | | | 606/199 |
| 2008/0078030 A1* | 4/2008 | Lee | A61B 5/11 |
| | | | 5/616 |
| 2010/0139005 A1 | 6/2010 | Perez | |
| 2013/0061445 A1* | 3/2013 | Allen | A61B 50/20 |
| | | | 29/428 |
| 2013/0318714 A1 | 12/2013 | Yu | |
| 2014/0130260 A1* | 5/2014 | Kreuzer | A61G 13/1245 |
| | | | 5/624 |
| 2015/0305735 A1* | 10/2015 | Gorek | A61B 17/06161 |
| | | | 606/147 |

\* cited by examiner

SUPPORT DEVICE FOR PERCUTANEOUS INTERVENTION

RELATED APPLICATION

This application claims priority to Italy Patent Application No. RM2014A000371, filed on Jul. 9, 2014, the entire contents of which are incorporated herein by reference.

FIELD

The present disclosure relates to a medical device. More specifically, the present disclosure relates to a medical support device for percutaneous interventional procedures.

BACKGROUND

The statements in this section merely provide background information related to the present disclosure and may or may not constitute prior art.

In recent years percutaneous interventions have shown an exponential growth in number as well complexity of the performed procedures. The medical devices employed during these procedures are very often about 1 to 3 meters in length but are commonly less than one millimeter in thickness. Therefore, careful manipulation of these devices is required to avoid damaging their fragile structure during positioning maneuvers.

In general, the medical devices are held in place by the operator, such as a physician, with the help of one or more assistants using the patient legs as an uneven support surface. Such an arrangement may prevent the operator to fully focus on the critical aspects of the interventional procedure. Moreover, the lack of a large flat support surface increases the likelihood of twisting or damaging one or more of the devices being employed simultaneously, thus potentially prolonging the procedural time and increasing the likelihood of complications.

SUMMARY

In view of the above mentioned drawbacks of currently available support devices, there is a need for a support device that supports various medical devices associated with percutaneous interventional procedures.

In one aspect, the device includes a support body with a substantially "C" squared-shape. The support body includes a support member and upright elements arranged on opposite sides of the support member that extend substantially orthogonally from the support member toward a surgical table. The device further includes one or more adjustment mechanisms connected to respective upright elements that adjust the spacing of the support member with respect to the surgical table to accommodate a patient's body positioned on the surgical table.

The device may provide one or more of the following advantages. For example, the device can be a large flat surface that helps the operator to hold various medical devices in place, which makes the procedure easier to perform. Further, the support device allows the operator to comfortably manipulate long and thin medical devices, thus lowering the risk of these medical devices from twisting and avoiding the use of a part of the patient's anatomy as an uneven support surface. The support device is adjustable to accommodate different body sizes. Manufacturing the support device from plastic may result in a lighter and less expensive device.

Further features, advantages, and areas of applicability will become apparent from the description provided herein. It should be understood that the description and specific examples are intended for purposes of illustration only and are not intended to limit the scope of the present disclosure.

DRAWINGS

Figure 2:
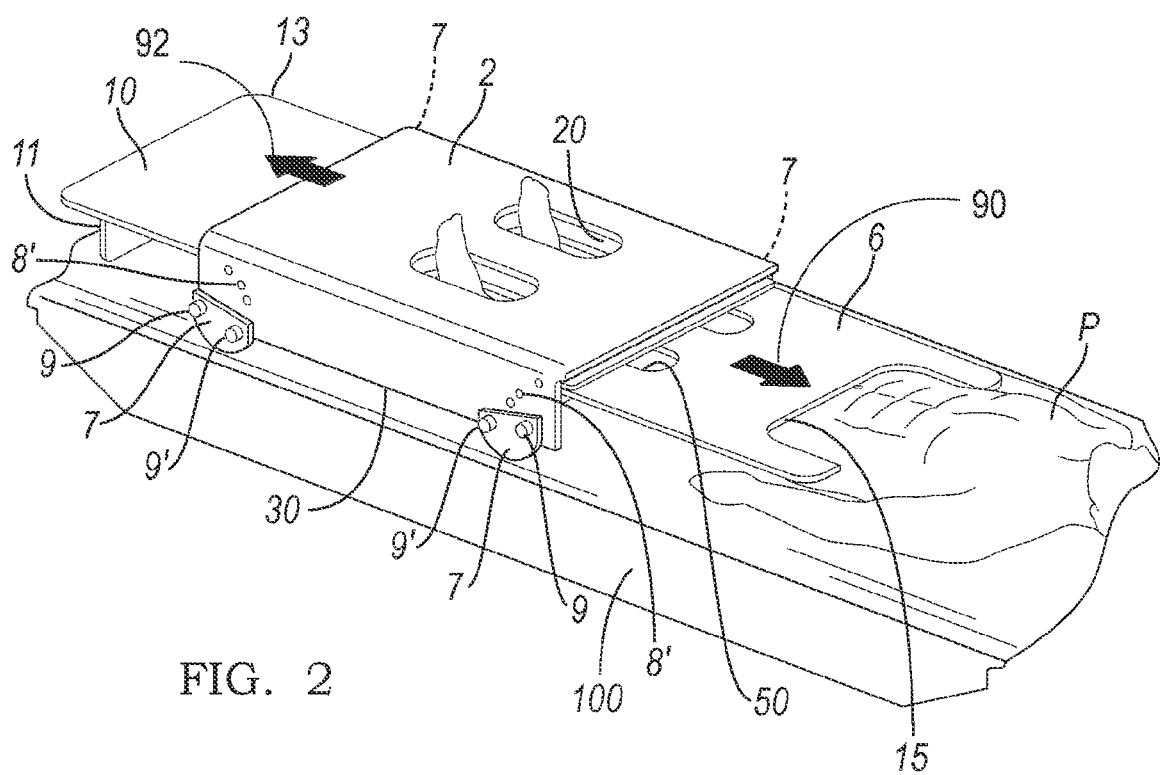

The drawings described herein are for illustration purposes only and are not intended to limit the scope of the present disclosure in any way. The components in the figures are not necessarily to scale, emphasis instead being placed upon illustrating the principles of the invention. Moreover, in the figures, like reference numerals designate corresponding parts throughout the views. In the drawings:

FIG. 1 shows a perspective view of a support device for interventional procedures in accordance with the principles of the present invention; and FIG. 2 shows the support device of FIG. 1 in use during an interventional procedure.

DETAILED DESCRIPTION

The following description is merely exemplary in nature and is not intended to limit the present disclosure, application, or uses.

Referring now to the drawings, a support device embodying the principles of the present invention is shown in FIGS. 1 and 2 and designated at 1. The support device 1 is configured to support various medical devices above the body of a patient, P, in lying in a supine position on a surgical table during the execution of percutaneous interventional procedures.

The support device 1 includes a support member 2 and upright elements 3. As such, the support device 1 has a substantial "C" squared shaped support body 1'. In various arrangements, the support device 1 has a laminar structure with an internal side that covers the patient's body and an external side which support one or more medical devices. For such arrangements, the support device 1 device can be manufactured or formed from a single laminar component with the upright elements 3 arranged on the opposite sides of the support member 2 with a substantially orthogonal orientation.

Each upright element 3 provides support for a support base 30 on the surgical table 100 and is shaped for spacing the support member 2 from the surgical table 100 during the procedures. The upright elements 3 include adjustment mechanisms 7 that adjust the spacing of the support member 2 to accommodate the patient, P, positioned or to be positioned between the support member 2 and the surgical table 100.

The support device 1 includes one or more openings 20 that are shaped to allow the insertion at least a part of the patient's feet, specifically the part of the feet with toes. This configuration helps to prevent unwanted movement of the patient's legs.

The adjustment mechanisms 7 are configured to vary the distance of their external ends 7' from a chosen fixed point by the use of different rotation angles. In the arrangement shown in FIGS. 1 and 2, the adjustment mechanisms 7 are half-moon shaped and are secured to the upright elements 3 with connectors 9 and 9' near each of the outer corners of the upright elements 3. The connectors 9 and 9' can be, for example, screws and pins or any other suitable connecting device that may be removable. Specifically, each adjustment mechanism includes two holes that receive the two connectors 9 and 9' to secure the adjustment mechanism to a respective upright element 3.

In certain arrangements, each upright element 3 has at least one seat to receive respective connectors 9 and/or 9'. In the example shown, the support base 30 includes at each extremity, for example, near each of the outer corners of the upright elements 3, a first opening 8 that receives the fixed connector 9 and one or more openings 8' that receive the connector 9'. The openings 8' can be spaced along a half ring path to provide variable heights of the support base 30 with respect to the surgical table 100. Accordingly, the height of the upright elements 3 is set by adjusting the distance of the support base 30 from the surgical table 100 through the rotation of the half-moon portion of the adjustment mechanisms 7 about the fixed connectors 9.

Hence, after the device 1 has been positioned over the patient's body, the distance between the support member 2 and the surgical table 100 is adjusted with the adjustment mechanisms 7 according to the patient's body characteristics, thus stabilizing the support device 1 on the surgical table 100 while avoiding placing pressure on the patient's body with the support device 1. After the desired spacing is obtained, the half-moon portion of the adjustment mechanisms 7 are fixed to the upright elements 3 with the connectors 9' secured at the particular openings 8'. The adjustment means 7 can be set to provide the same spacing at each location. One or more adjustment mechanisms 7 can be set to different spacings.

In another arrangement, each adjustment mechanism 7 is set with a single connector, such as, for example, a lockable pin or screw. The rotation of the half-moon portion of each adjustment mechanism 7 about the connector axis provides adjustment of the spacing of the support base 30 from the surgical table 100.

The support device 1 can include a cranial member 6 that covers a part of the patient's body during an interventional procedure. As shown, the contour of the cranial member 6 can have an ergonomic shape, such as, for example, a portion 15 oriented to the patient's abdomen. The portion 15 has a "U" shape to allow simultaneous radial and femoral vascular access. Another portion 50 of the cranial member 6 has a double "U" shape to avoid interference with the patients' feet extending through the openings 20.

The cranial member 6 is able to slide with respect to the support member 2, as indicated by the arrow 90, such that it can be inserted under the support member 2 when not in use (for example, between procedures), which being easily pulled out during procedures. In certain arrangements, the support body 1' includes sliding guides 4 positioned, for example, internally on the upright elements 3 to allow sliding movement of the cranial member 6 with respect the support member 2.

The support device 1 also includes a caudal member 10 to support one or more medical devices during percutaneous interventional procedures. The support body 1' also includes sliding guides 40 spaced from and extending parallel to sliding guides 4 positioned, for example, internally on the upright elements 3 to allow sliding movement of the caudal member 10 with respect the support member 2 as indicated by the arrow 92. The caudal member 10 can be inserted under the supporting surface 2 when not in use or the caudal member can be pulled out during use of the support device 1.

In some arrangements, the caudal member 10 has at its caudal end one more upright components 11 oriented in a substantially orthogonal direction with respect a main surface 13. This upright element 11 is positioned to support the member 10 when in use to avoid unwanted deformation of the member 10 that could result when medical devices are placed on the surface 13. Accordingly, in various arrangements, the support device 1 provides a large, hard and flat working surface positioned over the surgical table 100 and partially over the patient's body that facilitates optimal manipulation of the medical devices and to prevent damaging the devices.

The support device 1 can be made from plastic material, or any other suitable material, with appropriate hardness, lightness and radiolucency. The support device 1 can be employed with any interventional operating or surgical table for various procedures such as for cardiology, radiology or vascular surgery etc. The support device 1 can be quickly installed and adjusted.

The support device 1 may include various components supplied as an assembly kit to be assembled in the support device.

Various components of the support device 1 can be constructed with radiolucent material to allow free transmission of X-rays to the patient for aiding the interventional procedure.

The description of the invention is merely exemplary in nature and variations that do not depart from the gist of the invention are intended to be within the scope of the invention. Such variations are not to be regarded as a departure from the spirit and scope of the invention.

What is claimed is:

1. A device to support one or more medical devices above a patient in a supine position on a surgical table during a percutaneous interventional procedure, the device comprising:
   a support body with a substantially "C" squared-shape, the support body having a support member and upright elements arranged on opposite sides of the support member that extend substantially orthogonally from the support member toward the surgical table, the support body having one or more openings to allow insertion of at least one part of the patient's feet; and
   one or more adjustment mechanisms connected to respective upright elements that adjust the spacing of the support member with respect to the surgical table to accommodate the patient's body positioned on the surgical table.

2. The device of claim 1 wherein the body has a substantially laminar structure.

3. The device of claim 1 wherein each adjustment mechanism includes a half-moon shaped portion.

4. The device of claim 1 wherein each adjustment mechanism includes one or more connectors that secure the adjustment mechanism to the upright element.

5. The device of claim 4 wherein each upright element includes at least one seat that receives a respective connector.

6. The device of claim 1 further comprising a cranial member that covers a portion of the patient's body during the procedure.

7. The device of claim 6 wherein the support body includes one or more sliding guides that facilitates sliding the cranial member relative to the support member.

8. The device of claim 1 further comprising a caudal member that supports one or more medical devices during the procedure.

9. The device of claim 8 wherein the support body includes one or more sliding guides that facilitates sliding the caudal member relative to the support member.

10. The device of claim 1 wherein the support body and the one or more adjustment mechanisms are provided as an assembly kit.

\* \* \* \* \*